United States Patent [19]

Bundy

[11] 4,211,706
[45] Jul. 8, 1980

[54] 9-DEOXY-9α,6-NITRILO OR 6,9α-IMINO-17,18-DIDEHYDRO-PGF COMPOUNDS

[75] Inventor: Gordon L. Bundy, Portage, Mich.

[73] Assignee: The Upjohn Company, Kalamazoo, Mich.

[21] Appl. No.: 951,095

[22] Filed: Oct. 13, 1978

[51] Int. Cl.$^2$ .......................................... C07D 209/52
[52] U.S. Cl. ............................ 260/326.27; 260/244.4;
542/416; 542/421; 542/422; 542/426; 542/429;
542/430; 542/431; 544/143; 544/144; 544/362;
544/364; 544/373; 546/183; 546/194; 546/200;
546/201; 546/272; 546/256
[58] Field of Search .............. 542/426, 421, 416, 422,
542/429, 430, 431; 260/326.27, 293.56, 293.61,
295 S, 295 K; 544/143, 144, 373, 362, 364;
546/183, 193, 200, 201

[56] References Cited

U.S. PATENT DOCUMENTS

| 4,097,489 | 6/1978 | Bundy | 542/429 |
| 4,104,474 | 8/1978 | Smith | 260/563 |
| 4,136,095 | 1/1979 | Bundy | 542/429 |

OTHER PUBLICATIONS

Bundy et al., Chem. Abst. 89(1978) #129081, abstract of Tet. Let., 1978 (Apr.) #16, pp. 1371–1374.

Primary Examiner—Arthur P. Demers
Attorney, Agent, or Firm—Robert A. Armitage

[57] ABSTRACT

The present invention relates to certain structural and pharmacological analogs of cis-17,18-didehydroprostacyclin (PGI$_3$) wherein a nitrogen atom is substituted for 6,9α-epoxy-oxygen of prostacyclin. These novel nitrogen containing prostacyclin-type compounds are useful for the same pharmacological purposes for which prostacyclin is used, especially as antithrombotic agents.

2 Claims, No Drawings

9-DEOXY-9a,6-NITRILO OR 6,9a-IMINO-17,18-DIDEHYDRO-PGF COMPOUNDS

BACKGROUND OF THE INVENTION

The present invention relates to novel structural and pharmacological analogs cis-17,18-didehydroprostacyclin (PGI$_3$). In particular, the present invention relates to prostacyclin-type compounds wherein the 6,9α-epoxy-oxygen of prostacyclin is replaced by a nitrogen atom. Cis-17,18-didehydroprostacyclin exhibits the following structure and carbon atom numbering:

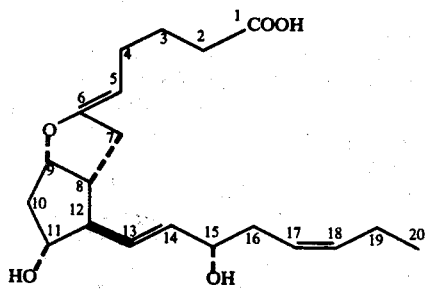
I

For discussion of prostacyclin, its biological activities, its methods of chemical synthesis, and the conventions for depicting formulas of such compounds, see U.S. Pat. No. 4,097,489, issued June 27, 1978, the relevant disclosure of which is incorporated here by reference. Also incorporated by reference from U.S. Pat. No. 4,097,489 are the conventions of nomenclature employed therein, especially those described on columns 2 and 6-12.

SUMMARY OF THE INVENTION

The present invention particularly comprises:
A prostacyclin analog of the formula

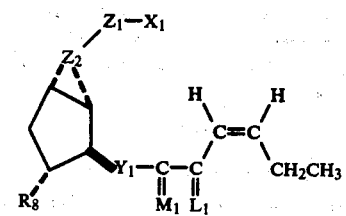
II wherein $Z_2$ is

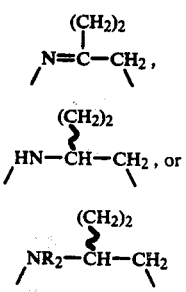

wherein
$R_2$ is alkyl of one to 4 carbon atoms, inclusive, or alkylcarbonyl of one of 4 carbon atoms, inclusive;

wherein
$Z_1$ is
(1) —(CH$_2$)$_g$—CH$_2$—CH$_2$—,
(2) —(CH$_2$)$_g$—CH$_2$—CF$_2$—, or
(3) trans—(CH$_2$)$_g$—CH=CH—,
wherein
g is the integer zero, one, or 2;
wherein
$R_8$ is hydrogen, hydroxy, or hydroxymethyl;
wherein
$Y_1$ is
(1) trans—CH=CH— or
(2) —CH$_2$CH$_2$—,
wherein
$M_1$ is

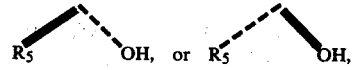

wherein
$R_5$ is hydrogen or alkyl with one to 4 carbon atoms, inclusive, wherein $L_1$ is

a mixture of

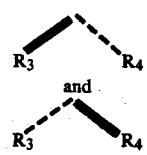

wherein $R_3$ and $R_4$ are hydrogen, methyl, or fluoro, being the same or different, with the proviso that one of $R_3$ and $R_4$ is fluoro only when the other is hydrogen or fluoro;
wherein $X_1$ is
(1) —COOR$_1$ wherein $R_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

 (a)

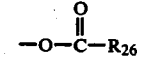 (b)

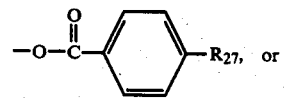 (c)

 (d)

wherein $R_{25}$ is methyl, phenyl, acetamidophenyl, benzamidophenyl, or —NH$_2$; $R_{26}$ is methyl, phenyl, —NH$_2$, or methoxy; and $R_{27}$ is hydrogen or acetamido; inclusive, or a pharmacologically acceptable cation;
(2) —CH$_2$OH; or (3) —COL$_4$, wherein L$_4$ is
  (a) amino of the formula —NR$_{21}$R$_{23}$, wherein R$_{21}$ and R$_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy, carboxy, alkoxycarbonyl of one to 4 carbon atoms, inclusive, or nitro; carboxyalkyl of one to four carbon atoms, inclusive; carbamoylalkyl of one to four carbon atoms, inclusive; cyanoalkyl of one to four carbon atoms, inclusive; acetylalkyl of one to four carbon atoms, inclusive; benzoylalkyl of one to four carbon atoms, inclusive; benzoylalkyl substituted by one, 2, or 3 chloro, alkyl of one to 3 carbon atoms inclusive; hydroxy, alkoxy of one to 3 carbon atoms, inclusive; carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl of one to 4 carbon atoms, inclusive; pyridylalkyl substituted by one, 2, or 3 chloro, alkyl of one to 3 carbon atoms, inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms, with the further proviso that not more than one of R$_{21}$ and R$_{22}$ is other than hydrogen or alkyl;
  (b) cycloamino selected from the group consisting of

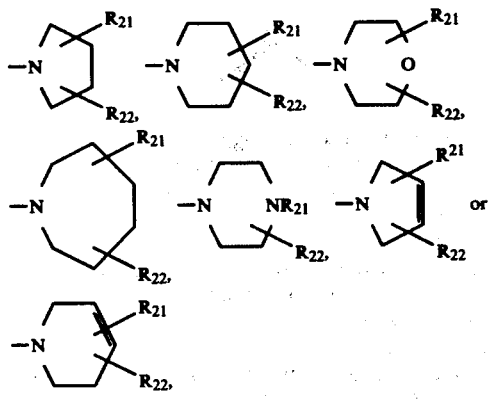

wherein R$_{21}$ and R$_{22}$ are as defined above;
  (c) carbonylamino of the formula —NR$_{23}$COR$_{21}$, wherein R$_{23}$ is hydrogen or alkyl of one to 4 carbon atoms and R$_{21}$ is as defined above; or
  (d) sulphonylamino of the formula —NR$_{23}$SO$_2$R$_{21}$, wherein R$_{21}$ and R$_{23}$ are as defined above; and the pharmacologically acceptable acid addition salts thereof when R$_2$ is not alkylcarbonyl and R$_1$ is not a pharmacologically acceptable cation.

With respect to the various preferred compounds from those described above, see the preferences and named species in U.S. Pat. No. 4,097,489. Also, with respect to the methods of using the compounds of the instant invention as pharmacological agents, especially as platelet aggregation inhibitors, see columns 12–19 of U.S. Pat. No. 4,097,489. The novel compounds of the instant invention are employed as pharmacological agents for the same pharmacological purposes and in the same manner as the novel prostaglandin analogs described in U.S. Pat. No. 4,097,489. Accordingly, when the novel compounds of the present invention are employed as platelet aggregation inhibitors, these compounds are used in patients (humans) for the treatment and prevention of myocardial infraction and the prevention of post-operative thrombosis, as well as agents for the maintenance of the patency of vascular grafts following surgery. Intravenous dosages of compounds in accordance with the present invention are from about 0.01 to 10 mg. per kg. of body weight per day intravenously, with the exact dose being determined by the attending physician depending on the age, weight, condition and route of administration selected for the patient. Compounds of the present invention are especially preferred as oral antithrombotic agents, being formulated in conventional oral dosage forms, e.g., tablets and capsules, for administration two to four times daily. Oral dosages of about 0.05 to 100 mg. per kg. of body weight per day are effective in the oral use of these compounds.

The compounds of the present invention are all prepared from the corresponding PGF$_3\beta$ compounds by the method depicted in Chart A (columns 20–21) of U.S. Pat. No. 4,097,489. This chart and discussion relating thereto are incorporated here by reference.

DESCRIPTION OF THE PREFERRED EMBODIMENTS

The preparation and use of compounds in accordance with the present invention is undertaken in accordance with procedures described in U.S. Pat. No. 4,097,489, the relevant disclosure which is incorporated here by reference, using PGF$_3\alpha$ or PGF$_3\beta$ starting material.

By virtue of the unsaturation at the C-17–C-18 position, compounds of the instant invention are all named as "cis-17,18-didehydro-PGF$_1$" compounds. Moreover, these compounds are prepared by methods analogous to those in Chart A, employing the PG$_3$ compound corresponding to the cis-17,18-didehydro-PGF$\alpha$ compound desired in accordance with the instant invention.

Accordingly, the following example is representative of the preparation of the compounds in accordance with the instant invention:

EXAMPLE 1

9-Deoxy-9a,6-nitrilo-cis-17,18-didehydro-PGF$_1$ (Formula II: X$_1$ is COOH, Z$_1$ is —(CH$_2$)$_2$—, Z$_2$ is

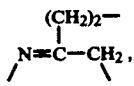

R$_8$ is hydroxy, Y$_1$ is trans—CH=CH—, R$_5$ of M$_1$ moiety and R$_3$ and R$_4$ of L$_1$ moiety are hydrogen).

A. Under a nitrogen atmosphere, with the exclusion of moisture, 352 mg. of PGF$_3\alpha$, methyl ester, is dissolved in 2 ml. of dimethylformamide and a mixture of t-butyldimethylsilylchloride, imidazole, in dimethylformamide (317 mg., 286 mg., and 2 ml., respectively) in 0° C. is added. After continuous stirring for 6 hr. at 0° C. the reaction exhibits partial completion and is thereafter allowed to stir for 15 hr. at ambient temperature. Thereafter the crude reaction mixture is washed with brine, extracted with 15% ethylacetate in hexane, and the organic extract washed again with brine and water and brine. After drying over magnesium sulfate and concentration under reduced pressure, the resulting residue (506 mg.) is chromatographed on 80 g. of silica gel packed with 5% ethyl acetate in hexane. Elution with 15% ethyl acetate in hexane yields 250 mg. of pure PGF$_3\alpha$, methyl ester, 11,15-bis(t-butyl-dimethylsilyl ether).

B. The reaction product of part A is dissolved in triphenylphosphine (235 mg.) benzoic acid (109 mg.) and tetrahydrofuran (5 ml.). After cooling in an ice-bath diethylazodicarboxylate (156 mg.) in 1 ml. of tetrahydrofuran is added. After stirring at 0° C. until silica gel TLC analysis indicates the reaction to be complete, the resulting mixture is chromatographed on 20 g. of silica gel, packed with 5% ethyl acetate in hexane and eluted with 5% ethylacetate in hexane to yield 204 mg. of PGF$_3\beta$, methyl ester, 11,15-bis(t-butyl-dimethylsilyl ether), 9-benzoate.

C. The reaction product of Part B (204 mg.) in methanol (5 ml.) is combined with 25% sodium methoxide and (0.75 ml.) in methanol under nitrogen atmosphere at ambient temperature. After stirring for 4 hr., the resulting mixture is poured into ice, water, and 20% ethylacetate in hexane. The organic phase is then washed twice with brine and concentrated at reduced pressure to yield 166.7 mg. of pure PGF$_3\beta$, methyl ester, 11,15-bis(-tetrahydropyranyl ether).

D. Reaction product of Part C (166.7 mg.) in 0.851 ml. of dry pyridine combined in ambient temperature with 0.090 g. of p-toluenesulfonyl chloride and the resulting mixture stirred at ambient temperature for 18 hr. Thereafter the mixture is cooled to 0° C. and 5 ml. of water is added with stirring for 10 min. Thereafter the reaction mixture is poured into an ice-brine mixture and extracted with 10% ethylacetate and hexane. The organic extracts are then washed with water and cold dilute sodium bisulfate (until acidic) and thereafter with sodium bicarbonate and brine. After drying over sodium sulfate, concentration under reduced pressure yields 166 mg. of PGF$_3\beta$, methyl ester 11,15-bis-(t-butyl-dimethylsilyl ether), 9-tosylate.

E. The reaction product of Part D (166 mg.), tetrahydrofuran (1.702 ml.), water (1.702 ml.) and acetic acid (5.1 ml.) are stirred at 40° C. for 9 hr., whereupon the resulting mixture is poured into brine and water (1:1) and extracted with ethyl acetate and hexane (1:1). The organic extracts are carefully washed with sodium bicarbonate until basic pH (pH 9) is obtained, and thereafter with brine. After drying over sodium sulfate and concentrating under reduced pressure, a residue (160 mg.) of PGF$_3\beta$, methyl ester, 9-tosylate, is obtained.

F. The reaction product is Part E (160 mg.) and 10 ml. of hexamethylphosphoramide and 1 g. of sodium azide are stirred under a nitrogen atmosphere at 40° C. for 2 hr., followed by cooling in an ice-bath. Therafter the resulting cooled mixture is poured into a mixture of ice, brine, and water and extracted with diethyl ether. The etheral extracts are then washed with water and brine, dried over sodium sulfate, and concentrated under reduced pressure to yield a residue of 9-deoxy-9$\alpha$-azido-PGF$_3\alpha$, methyl ester.

G. The reaction product of Part F (150 mg.) in methanol (5 ml.) is cooled to 0° C. and 5 ml. of 3 normal potassium hydroxide is added. Thereafter the ice-bath is removed and the resulting mixture is stirred at ambient temperature for 3 hr. The resulting compound, crude 9-deoxy-9-azido-PGF$_3\alpha$, is then poured into a mixture of ice and water and 10 ml. of 2 N potassium bisulfate is added and the resulting mixture extracted with ethyl acetate. The organic extracts are then washed with brine, dried over magnesium sulfate and concentrated under reduced pressure to yield a residue. This residue is then dissolved in 40 ml. of ethyl acetate and heated to 80° C. for 16 hr. Thereupon the mixture is concentrated under reduced pressure and chromatographed on 15 g. of acid-washed silica gel packed with 30% methanol in ethyl acetate and eluted with 30% methanol in ethyl acetate. Filtration through cotton and drying yields 12 mg. of pure title product, 9-deoxy-9$\alpha$,6-nitrilo-PGF$_3$. Silica gel TLC r$_f$ is 0.29 in ethyl acetate, methanol, in acetic acid (65:35:1). Infrared absorptions observed at 3400, 1720, 1635, 1260, 1200, 1130, 1070, 970 cm$^{-1}$. The mass spectrum for the trimethylsilyl derivative exhibits a weak molecular ion at 565 and a demethylated high resolution ion at 550.3229.

EXAMPLE 2

9-Deoxy-9$\alpha$,6-nitrilo-cis-17,18-didehydro-PGF$_1$, methyl ester.

The title product of Example 1 is dissolved in ethereal diazomethane at ambient temperature, whereby crude title product is obtained by concentration under reduced pressure. Purification on silica gel yields pure title product.

Following the procedures of Examples 1 and 2, but employing the various other PGF$_3\alpha$ and PGF$_3\beta$ starting materials corresponding to a desired formula I product, there are prepared in free acid or methyl ester form each of the various corresponding 9-deoxy-9$\alpha$, 6-nitrilo-cis-17,18-didehydro-PGF$_1$ compounds.

EXAMPLE 3

(6R)- and (6S)-deoxy-6,9$\alpha$-imino-cis-17,18-didehydro-PGF$_1$, methyl ester.

A solution of 2.5 g of the title product of Example 2 in 60 ml of dry methanol is stirred at ambient temperature and treated thereafter with 500 mg of sodium borohydride. After 1 hr of continued stirring at ambient temperature, a mixture of (6RS) products is obtained. This mixture is then poured into ice and brine, extracted with ethyl acetate, and the ethyl acetate extracts washed with brine, dried over sodium sulfate and concentrated under reduced pressure. Crude product is then chromatographed on silica gel eluting with a mixture of methanol, chloroform, and triethylamine (10:90:2). Accordingly there are obtained the (6R) isomer. Further there is obtained the (6S)-isomer, being the more polar of the two isomers by TLC.

Following the procedure of Example 3, by employing each of the various 9-deoxy-9,6$\alpha$-nitrilo-cis-17,18-didehydro-PGF-type compounds described following Example 2 in place of 9-deoxy-9,6$\alpha$-nitrilo-cis-17,18-didehydro-PGF$_2$ as employed in Example 3, there are obtained each of the various (6R) or (6S)-9-deoxy-6,9$\alpha$-imino-cis-17,18-didehydro-PGF$_1$-type compounds.

EXAMPLE 4

(6R)-9-deoxy-6,9$\alpha$-imino-cis-17,18-didehydro-PGF$_1$.

The title product of Example 3 (500 mg) in 3 ml of methanol is added to 3 ml of 1 N potassium hydroxide under a nitrogen atmosphere and stirred for 18 hrs at ambient temperature. Thereafter the methanol is removed under reduced pressure and the resulting product diluted with water (2 ml) and acidified to pH 6.0 with dilute aqueous hydrochloric acid.

The resulting mixture is then lyophilized and the residue taken up in 3 ml of water and chromatographed on a 50 ml column of a neutral (i.e., non-basic and non-acidic) resin. Elution with water and methanol yields the title product in the methanolic fractions. This product is then concentrated under reduced pressure and the residue dissolved in 15 ml of water and lyophilized yielding crude product.

The crude product in 50 ml of diethyl ether is then allowed to stand at ambient temperature for 60 hrs. Thereafter the product is filtered, washed with fresh diethyl ether, and dried under a nitrogen atmosphere, yielding pure title product.

Following the procedure described above the (6S) isomer yields (6S)-9-deoxy-6,9α-imino-cis-17,18-didehydro-PGF$_1$.

EXAMPLE 5

9-Deoxy-9α,6-nitrilo-cis-17,18-didehydro-PGF$_1$, hydrochloride.

The title product of Example 1 (700 mg) in 20 ml of water is mixed with stirring with 20 ml of aqueous 0.1 N hydrochloric acid. The mixture is lyophilized and the residue treated with 50 ml of anhydrous tetrahydrofuran. On stirring, title product is obtained.

EXAMPLE 6

N-Methyl-(6R)-9-deoxy-6,9α-imino-cis-17,18-didehydro-PGF$_1$, methyl ester.

The title product of Example 3 is diluted in methanol and thereafter treated with a single stoichiometric equivalent of methyl iodide. The reaction mixture is then heated from ambient temperature to reflux for about 6 hrs.

As the reaction is shown to be complete, the reaction mixture is then cooled, made basic with dilute ammonium hydroxide (to pH 12). Title product is then obtained from the reaction mixture by extraction with ethyl acetate, washing the extracts, and concentrating the pure title product.

Following the procedure of Example 6, each of the various N-methyl products of formula I is obtained.

EXAMPLE 7

N-acetyl-(6R)-9-deoxy-6,9α-imino-PGF$_1$, methyl ester.

The title product of Example 3 in pyridine is reacted with excess acetic anhydride at ambient temperature and thereafter with methanolic sodium bicarbonate at ambient temperature for several days. When chromatographic analysis indicates the deesterification to be complete, the title product is recovered by conventional separation and purification techniques.

Following the procedure of Example 7, there are obtained each of the various formula I compounds wherein R$_2$ is acetyl.

Following the procedure of the above examples, but employing the the appropriate PGF$_2$β-type starting material, there are prepared
9-deoxy-9α,6-nitrilo-cis-17,18-didehydro-PGF$_1$-type compounds;
6α- or 6β-9-deoxy-6,9α-imino-cis-17,18-didehydro-PGF$_1$-type compounds; or
6R- or 6S-N-methyl- or N-acetyl-9-deoxy-6,9α-imino-cis-17,18-didehydro-PGF$_1$-type compounds
in free acid, amide, or ester form which exhibit the following side chain substituents:
15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
2,2-Difluoro-;
2,2-Difluoro-15-methyl-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
trans-2,3-Didehydro-;
trans-2,3-Didehydro-15-methyl-;
trans-2,3-Didehydro-16-methyl-;
trans-2,3-Didehydro-16,16-dimethyl-;
trans-2,3-Didehydro-16-fluoro-;
trans-2,3-Didehydro-16,16-difluoro-;
trans-2,3-Didehydro-13,14-dihydro-;
trans-2,3-Didehydro-16-methyl-13,14-dihydro-;
trans-2,3-Didehydro-16,16-dimethyl-13,14-dihydro-;
trans-2,3-Didehydro-16-fluoro-13,14-dihydro-;
trans-2,3-Didehydro-16,16-difluoro-13,14-dihydro-;
and their corresponding 11-deoxy-PGF$_1$ and 11-deoxy-11-hydroxymethyl-PGF$_1$ analogs.

Further, following procedures described above there are prepared the corresponding hydrochloride salts of each of the above compounds and the pharmacologically acceptable cations of compounds above in free acid form.

What is claimed is:

1. A prostacyclin analog of the formula

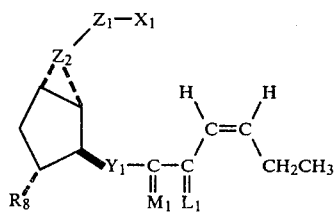

II wherein Z$_2$ is

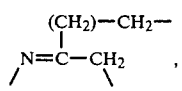

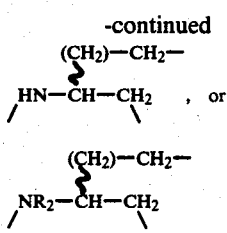, or wherein
R$_2$ is alkyl of one to 4 carbon atoms, inclusive, or alkylcarbonyl of one to 4 carbon atoms, inclusive;
wherein Z$_1$ is
(1) —(CH$_2$)$_g$—CH$_2$—CH$_2$—,
(2) —(CH$_2$)$_g$—CH$_2$—CF$_2$—, or
(3) trans—(CH$_2$)$_g$—CH=CH—,
wherein g is the integer zero, one, or 2;
wherein R$_8$ is hydrogen, hydroxy, or hydroxymethyl;
wherein Y$_1$ is
(1) trans—CH=CH— or
(2) —CH$_2$CH$_2$—,
wherein
M$_1$ is

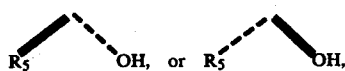

wherein
R$_5$ is hydrogen or alkyl with one to 4 carbon atoms, inclusive, wherein L$_1$ is

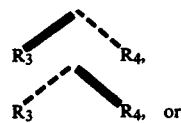

a mixture of

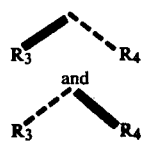

and
wherein R$_3$ and R$_4$ are hydrogen, methyl, or fluoro, being the same or different, with the proviso that one of R$_3$ and R$_4$ is fluoro only when the other is hydrogen or fluoro;
wherein X$_1$ is
(1) -COOR$_1$ wherein R$_1$ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by (a) —NH—ĊR$_25$ (b) —O—Ċ—R$_26$ (c) 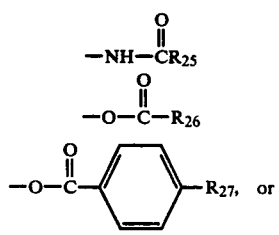

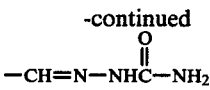

wherein R$_{25}$ is methyl, phenyl, acetomidophenyl, benzamidophenyl, or —NH$_2$; R$_{26}$ is methyl, phenyl, —NH$_2$, or methoxy; and R$_{27}$ is hydrogen or acetamido; inclusive, or a pharmacologically acceptable cation;
(2) —CH$_2$OH; or
(3) —COL$_4$, wherein L$_4$ is
(a) amino of the formula-NR$_{21}$R$_{23}$, wherein R$_{21}$ and R$_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy, carboxy, alkoxycarbonyl of one to 4 carbon atoms, inclusive, or nitro; carboxyalkyl of one to four carbon atoms, inclusive; carbamoylalkyl of one to four carbon atoms, inclusive; cyanoalkyl of one to four carbon atoms, inclusive, acetylalkyl of one to four carbon atoms, inclusive; benzoylalkyl of one to four carbon atoms, inclusive; benzoylalkyl substituted by one, 2, or 3 chloro, alkyl of one to 3 carbon atoms inclusive; hydroxy, alkoxy of one to 3 carbon atoms, inclusive; carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl of one to 4 carbon atoms, inclusive; pyridylalkyl substituted by one, 2, or 3 chloro, alkyl of one to 3 carbon atoms, inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms, with the further proviso that not more than one of R$_{21}$ and R$_{22}$ is other than hydrogen or alkyl;
(b) cycloamino selected from the group consisting of

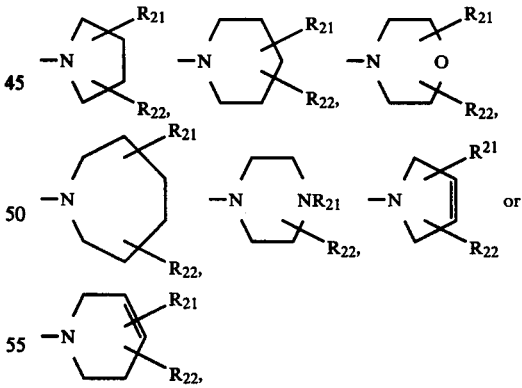

wherein R$_{21}$ and R$_{22}$ are as defined above;
(c) carbonylamino of the formula —NR$_{23}$COR$_{21}$, wherein R$_{23}$ is hydrogen or alkyl of one to 4 carbon atoms and R$_{21}$ is as defined above; or
(d) sulphonylamino of the formula —NR$_{23}$SO$_2$R$_{21}$, wherein R$_{21}$ and R$_{23}$ are as defined above; and the pharmacologically acceptable acid addition salts thereof when R$_2$ is not alkylcarbonyl and R$_1$ is not a pharmacologically acceptable cation.
2. 9-Deoxy-9α,6-nitrilo-cis-17,18-didehydro-PGF$_1$, a prostacyclin analog according to claim 1.

* * * * *

UNITED STATES PATENT OFFICE
CERTIFICATE OF CORRECTION

Patent No. 4,211,706      Dated 8 July 1980

Inventor(s) Gordon L. Bundy

It is certified that error appears in the above-identified patent and that said Letters Patent are hereby corrected as shown below:

Column 3, line 2, and Column 10, line 11, "$NR_{21}R_{23}$" should read -- $NR_{21}R_{22}$ --;

Column 8, lines 65-68, "
$$\begin{array}{c} (CH_2)-CH_2- \\ | \\ N=C-CH_2 \\ / \quad \backslash \end{array}$$
" should read --
$$\begin{array}{c} (CH_2) \\ | \\ N=C-CH_2 \\ / \quad \backslash \end{array}$$
-- ;

Column 9, lines 1-4, "
$$\begin{array}{c} (CH_2)-CH_2- \\ | \\ HN-CH-CH_2 \\ / \quad \backslash \end{array}$$
" should read --
$$\begin{array}{c} (CH_2) \\ | \\ HN-CH-CH_2 \\ / \quad \backslash \end{array}$$
-- ;

Column 9, lines 6-9, "
$$\begin{array}{c} (CH_2)-CH_2- \\ | \\ NR_2-CH-CH_2 \\ / \quad \backslash \end{array}$$
" should read --
$$\begin{array}{c} (CH_2) \\ | \\ NR_2-CH-CH_2 \\ / \quad \backslash \end{array}$$
-- .

Signed and Sealed this

*Twenty-eighth* Day of *April 1981*

[SEAL]

*Attest:*

RENE D. TEGTMEYER

*Attesting Officer*     *Acting Commissioner of Patents and Trademarks*